United States Patent
Mann

(10) Patent No.: US 6,558,539 B1
(45) Date of Patent: May 6, 2003

(54) SLURRY FILL METHOD AND VALVE

(76) Inventor: William H. Mann, 836 Belvoir Crest, Chattanooga, TN (US) 37412

(*) Notice: Subject to any disclaimer, the term of this patent is extended or adjusted under 35 U.S.C. 154(b) by 6 days.

(21) Appl. No.: 09/711,973

(22) Filed: Nov. 14, 2000

Related U.S. Application Data

(62) Division of application No. 09/410,156, filed on Sep. 30, 1999, now Pat. No. 6,190,560.

(51) Int. Cl.[7] .............................................. B01D 15/08
(52) U.S. Cl. .................................... 210/198.2; 210/656
(58) Field of Search ................................ 210/656, 659, 210/198.2, 281; 95/82; 96/101

(56) References Cited

U.S. PATENT DOCUMENTS

| | | | | |
|---|---|---|---|---|
| 3,966,609 A | * | 6/1976 | Godbille | 210/198.2 |
| 4,341,635 A | * | 7/1982 | Golias | 210/198.2 |
| 4,350,595 A | * | 9/1982 | Gunkel | 210/198.2 |
| 4,361,482 A | * | 11/1982 | Teetz | 210/198.2 |
| 4,470,910 A | * | 9/1984 | Quemerais | 210/198.2 |
| 4,497,711 A | * | 2/1985 | Shepherd | 210/656 |
| 4,578,193 A | * | 3/1986 | Shepherd | 210/656 |
| 4,597,866 A | * | 7/1986 | Couillard | 210/198.2 |
| 4,670,141 A | * | 6/1987 | Shackelford | 210/198.2 |
| 4,719,011 A | * | 1/1988 | Shalon | 210/198.2 |
| 4,769,141 A | * | 9/1988 | Couillard | 210/198.2 |
| 4,891,133 A | * | 1/1990 | Colvin | 210/198.2 |
| 5,021,162 A | * | 6/1991 | Sakamoto | 210/635 |
| 5,141,635 A | * | 8/1992 | LePlang | 210/198.2 |
| 5,158,676 A | * | 10/1992 | Kreher | 210/198.2 |
| 5,167,809 A | * | 12/1992 | Mann | 210/198.2 |
| 5,167,810 A | * | 12/1992 | Vassarotti | 210/198.2 |
| 5,169,522 A | * | 12/1992 | Shalon | 210/198.2 |
| 5,213,683 A | * | 5/1993 | Mann | 210/198.2 |
| 5,282,973 A | * | 2/1994 | Mann | 210/656 |
| 5,413,708 A | * | 5/1995 | Huse | 210/198.2 |
| 5,423,982 A | * | 6/1995 | Jungbauer | 210/198.2 |
| 5,462,659 A | * | 10/1995 | Saxena | 210/198.2 |
| 5,486,289 A | * | 1/1996 | McCollough | 210/198.2 |
| 5,667,675 A | * | 9/1997 | Hatch | 210/198.2 |
| 5,667,676 A | * | 9/1997 | Alaska | 210/198.2 |
| 5,866,008 A | * | 2/1999 | Shalon | 210/198.2 |
| 5,902,485 A | * | 5/1999 | Davis | 210/656 |
| 5,951,873 A | * | 9/1999 | Shalon | 210/198.2 |
| 6,117,317 A | * | 9/2000 | Dickson | 210/198.2 |
| 6,123,849 A | * | 9/2000 | Purdom | 210/198.2 |
| 6,190,560 B1 | * | 2/2001 | Mann | 210/656 |

* cited by examiner

*Primary Examiner*—Ernest G. Therkorn
(74) *Attorney, Agent, or Firm*—Alan Ruderman; Stephen J. Stark; Miller & Martin LLP

(57) ABSTRACT

A chromatography column has valve and method for filling it with a slurry of media, the valve utilizing a piston to compact the slurry in the column. The piston moves through a cavity in communication with both a slurry inlet and slurry ports which are in communication with the interior of the chromatography column. The piston assists in compacting the slurry within the column. The method of filling the column does not require disassembly of the column. The piston may also be utilized to change the valve position from a slurry fill position to a normal operation position or other position.

10 Claims, 3 Drawing Sheets

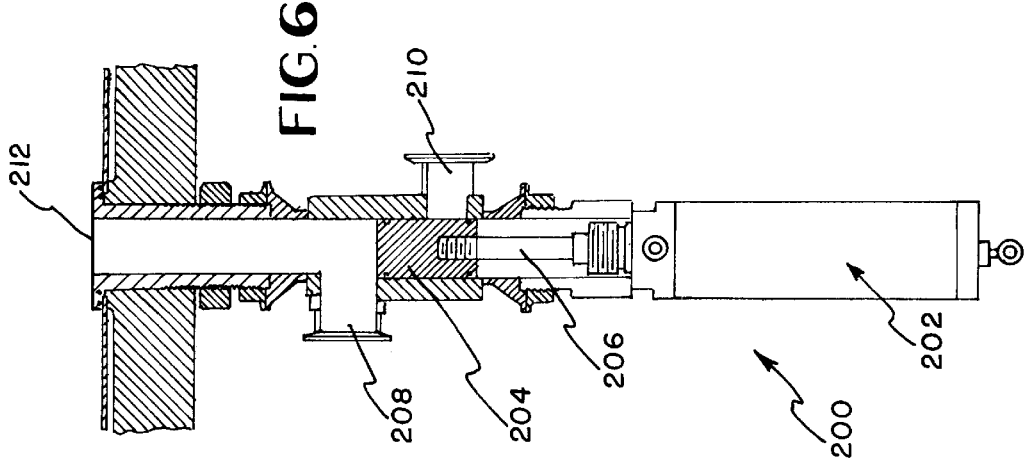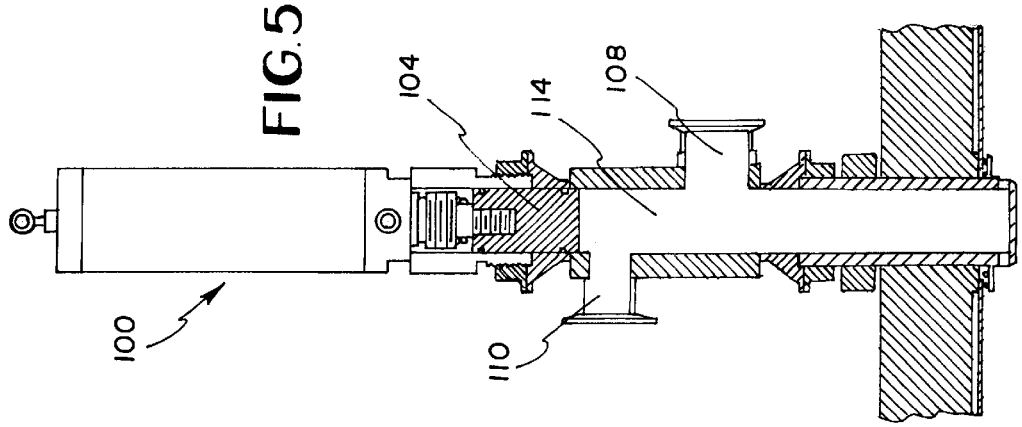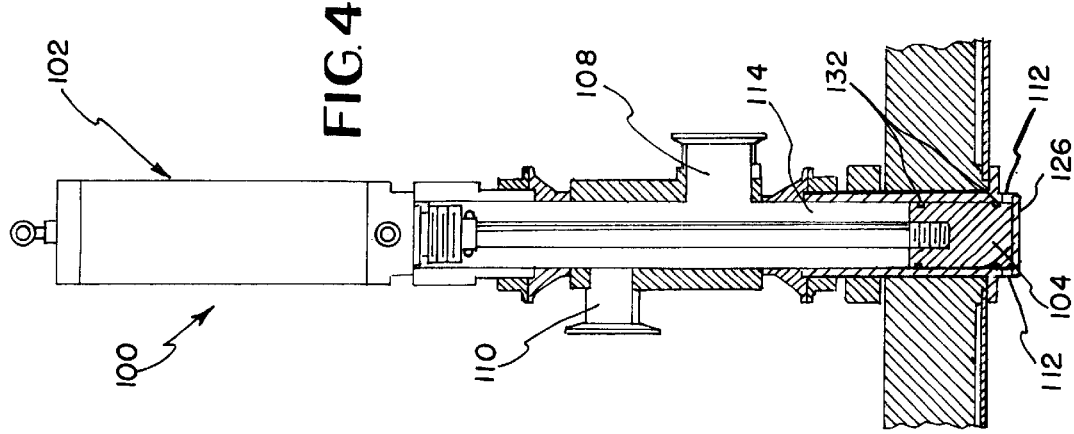

SLURRY FILL METHOD AND VALVE

REFERENCE TO RELATED APPLICATIONS

This application is a division of Ser. No. 09/410,156, filed Sep. 30, 1999, now U.S. Pat. No. 6,190,560.

BACKGROUND OF THE INVENTION

1. Field of the Invention

The present invention relates an apparatus and method of filling a container through a valve assembly and, more particularly, to such a valve assembly and the method for the charging of a fresh media bed in the form of a slurry into a chromatography column without disassembling the column. This valve assembly, or a similar valve assembly, may also be utilized to remove slurry from the chromatography column.

2. Description of Related Art

Chromatography is a process of separating the components of a mixture of chemical substances through the percolation of fluid through a body or bed of comminuted or porous rigid material, known as media. In the process, the various component are often resolved by their selective retardation as they are transported through the bed by a moving fluid or buffer. A solution of the substances to be separated becomes the moving phase of the system passing through the interstices in the stationary or continuous phase which are finely divided particles, possibly in the form of a gel slurry.

The substances in the moving phase are poured into the top of a chromatography column filled with the finely divided material, i.e., the media, that can absorb differentially the substances to be separated. The particular material used for the media varies widely with the substances to be separated. As the solution percolates down the column the components are separated from the buffer fluid which generally is pumped back into the top of the column so as to again pass down through the bed as a carrier. The different substances as they travel down the column at different rates form bands of the different substances which are individually collected at the outlet.

A chromatography column typically comprises a hollow vertically disposed cylindrical housing including a liquid dispensing section at the upper end and through which the buffer and substances to be separated are dispensed to the media bed, and a liquid collecting section at the lower end for collecting the substances and buffer individually. The media or bed through which the buffer fluid and mixture to be separated and purified percolates is located between these sections. The liquid dispensing section and liquid collecting section may each include a respective plate and at least one, and generally both, of the plates may be connected in an assembly with an axially movable plunger-like body positioned within the housing at the respective end. After the column is charged with the bed media, the bodies may be forced relatively to each other to compress and pressurize the media bed which has been poured into the column. Alternatively, a fixed bed media may not employ a plunger-like body to compress the media bed.

The known prior art methods for packing the bed of small diameter columns used for research and development, e.g., only a few inches in diameter, are fully disclosed in Sakamoto et al. U.S. Pat. No. 5,021,162 dated Jun. 4, 1991. In the conventional liquid flow method applicable to columns of larger diameter used in production of useful products such as synthetic insulin, e.g., approximately two feet in diameter, the bed media slurry is poured into a reservoir which has been temporarily connected to the upper end of the chromatography column. The reservoir is then closed at the top and liquid is pumped under pressure through the reservoir and the column. Excess liquid floating above the bed is pumped from the reservoir and the reservoir is then removed. This leaves part of the bed over-flowing above the top of the column, and the column is closed after this excess bed media is removed. In that method, as with most of the other prior art proposals discussed in the aforesaid patent, the top of the column must be disconnected in order to charge or pack the bed and must then thereafter be reassembled.

U.S. Pat. Nos. 5,213,683 and 5,282,973 disclose one method and apparatus for installing a slurry into a column. This reference discloses the use of a moveable inlet nozzle for inserting into the column for dispensing slurry into the column. The use of this type nozzle may create an impression in a media bed at the point where the nozzle contacts a fixed bed as the nozzle is retracted out of the media bed during operation. This creates a pooling of the product supplied to the column and may result in inefficient distribution of the product through the column. Accordingly, there is a need for an improved method and apparatus for filling a chromatography column.

SUMMARY OF THE INVENTION

The present invention recognizes and addresses these needs and others.

Consequently, it is an object of the present invention to provide a slurry fill method and apparatus in which the fill nozzle is stationary.

It is another object of the present invention to provide a compressed gas to assist in the packing of a chromatography column media bed.

It is still another object of the present invention to provide a fluid cylinder to assist in the packing of a media bed of a chromatography column.

It is yet another object of the present invention to provide a piston to alter the operational status of a valve assembly.

Accordingly, the present invention provides a chromatography column having a media and a product inlet assembly positioned at the inlet of a nozzle-type assembly at the top of the column, the media and product inlet assembly preferably including a housing having a product/buffer inlet passage and a media inlet passage extending through the housing. A piston having a pressurized fluid source is preferably connected to the housing to assist in the filling, distributing, and/or packing of the media bed within the column. Additionally, the piston may control the operational status of the slurry inlet assembly. A similar, or the same, valve may be utilized to remove slurry from a chromatography column as well.

BRIEF DESCRIPTION OF THE DRAWINGS

The particular features and advantages of the invention as well as other objects will become apparent from the following description taken in connection with the accompanying drawings in which:

FIG. 4 is a view similar to that illustrated in FIG. 3, but illustrated in a second position;

FIG. 5 is another view similar to FIG. 3, but illustrating the elements in a third position; and FIG. 6 is an enlarged fragmentary cross sectional view of the media removal section removed and broken away from the chromatography column shown in FIG. 1 in a slurry out position.

DETAILED DESCRIPTION OF THE PREFERRED EMBODIMENTS

Figure 1:
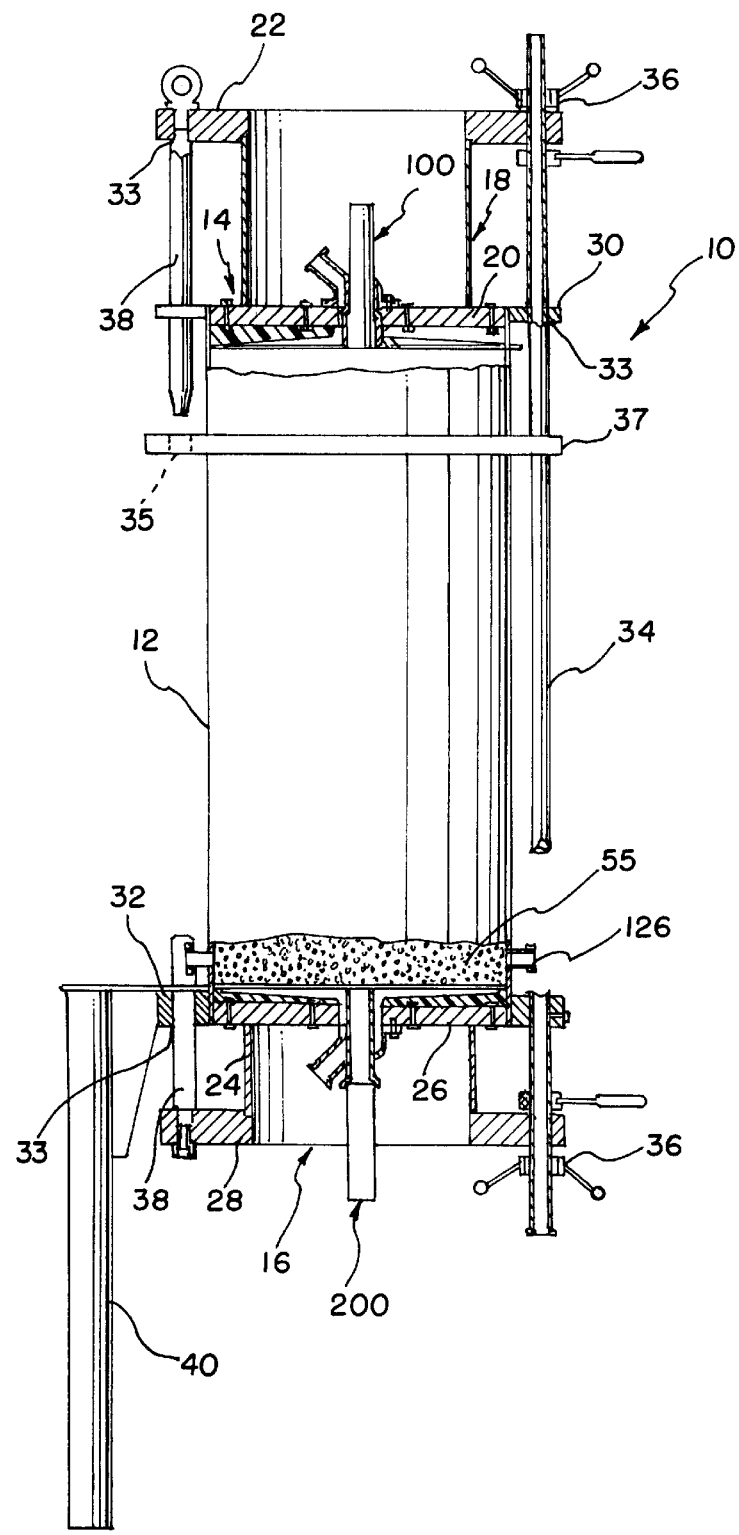
FIG. 1 is an elevation view, partly in cross section, of a prior art chromatography column with the media fill assembly removed.
Figure 2:
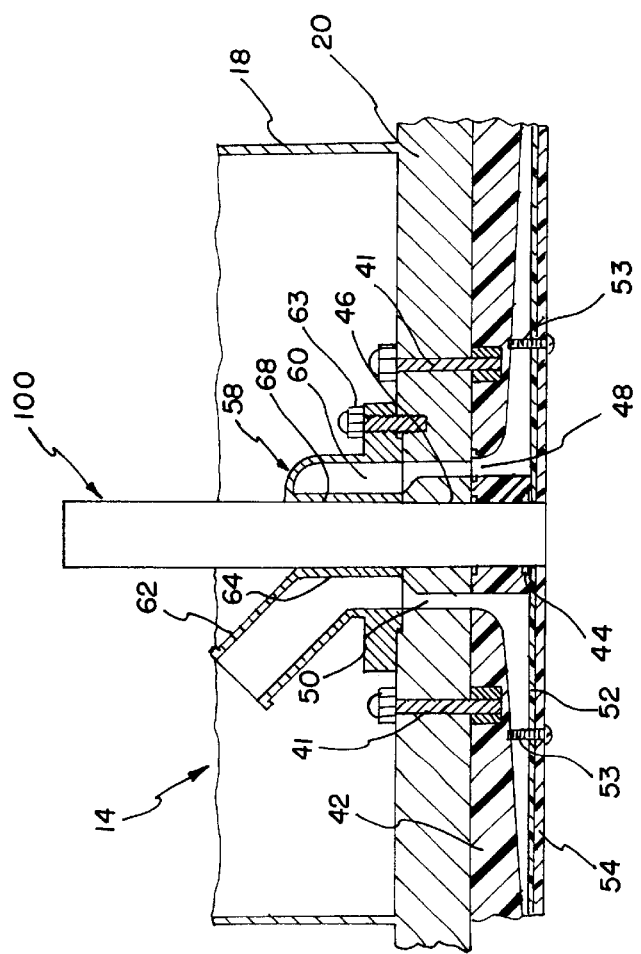
FIG. 2 is an enlarged fragmentary cross sectional view of the dispersion section of the chromatography column illustrated in FIG. 1.

The present invention is concerned with a method and apparatus for filling a chromatography column with a slurry and/or media, FIG. 1 depicting one such typical chromatography column 10 known in the art. The column 10 comprises an elongated hollow cylindrical housing 12 having a dispersion section 14 at the top and a collecting section 16 at the bottom, the housing preferably being constructed from stainless steel. The dispersion section 14 includes a hollow cylindrical elongated drum 18 having an upper cylindrical plunger head 20 formed at the lower end and a flange 22 formed at the top, the head 20 normally being disposed within the upper portion of the housing 12. The drum 18, plunger 20 and flange 22 also preferably are constructed from stainless steel and the plunger head and flange preferably are welded to the central drum 18. Likewise, the collection section 16 comprises a hollow cylindrical drum 24 having a lower cylindrical plunger head 26 being disposed within the lower portion of the housing. The column housing 12 includes an upper and lower ring or flange 30, 32 respectively welded thereto, the flanges 22, 28, 30 and 32 having a series of circumferentially spaced apart and aligned bores such as 33 for receiving a series of securing rods 34, only one of which is illustrated. The rods 34 have tightening members such as nuts or the like 36 threaded thereon at the remote top and bottom surfaces of the flanges 30 and 32 so as to draw the flanges 22 and 28 toward the column and thus move the plunger heads into the housing. Another flange 37 may also be welded to the column housing and has bores 35 through which the rods 36 are also received. Other rod members 38 receivable in certain of the bores may serve as legs for the dispensing and collecting section drums 18, 24 when disassembled from the column and act as guide rods when the drums are to be assembled to the column. Three or more legs 40, only one of which is illustrated, are welded to the flange 32 for positioning the column above the floor upon which it is mounted. The media filling valve assembly 100 of the column, which is illustrated as a box in both FIGS. 1 and 2, is shown in significantly more detail in FIGS. 3–5. A similar valve design is illustrated in FIGS. 1 and 6 as slurry outlet valve assembly 200. In FIG. 1, slurry outlet valve assembly 200 appears as a box, but is shown in more detail in FIG. 6.

Another variety of a typical chromatography column 10 in the prior art, which is not illustrated, is similar to the one shown in FIG. 1, except that plunger heads 20,26 are stationary and do not move towards one another. This type is commonly known in the art as a fixed bed column. These plunger heads 20,26 are preferably permanently mounted at top and bottom portions of the housing 12 in a fixed bed type column. Regardless of the type of column 10 utilized, the media filling method and apparatus taught herein will operate properly.

Dispersing sections are known in the art. One typical dispersing section is described herein, however other designs as known in the art could also be utilized. The details of the dispersing section may be understood with reference to FIG. 2. Thus, supported from the upper plunger head 20 by means of a plurality of bolts or screw members or the like 41 is a dispersion plate 42, the plate preferably being constructed from polypropylene or similar material. The dispersion plate 42 comprises a disk having a plurality of radially extending spaced apart ribs (not illustrated) disposed on the surface remote from the plunger head 20, i.e., the lower surface, and includes a central bore 44 which is aligned with a central bore 46 in the plunger head 20. A plurality of approximately 12 holes 48 are disposed in the plate 42 between the ribs spaced radially from the bore 44, while a similar series of holes 50 are disposed in the plate 42 between the ribs spaced radially from the bore 44, while a similar series of holes 50 are disposed in the plunger head 20 spaced radially from the bore 46 and aligned with the holes 48. Fastened to the underside of the dispersion plate is a perforated plastic support grid 52 which supports a sintered polyethylene filter 54, the support grid 52 and filter 54 being carried by the dispersion plate by means of screws 53 threaded into spaced apart ribs in the dispersion plate 42. Thus, as known in the art, the product and buffer liquid fed to the upper plunger head 20 flows through the holes 50 and 48 into the passages of the dispersion plate between the ribs, and is dispersed substantially uniformly onto the grid 52 and then onto the filter 54 where it is filtered and flows down into the media 55 in the housing 12. The grid 52 and filter 54 each have central bores aligned with the bore 44 of the plate 42 and a plastic annular nut 56 having a central bore 57 is received therethrough and threaded into the plunger head 20, an enlarged head 59 of the nut abutting the filter 54 to aid in securement of the members.

The column typically includes an inlet manifold housing 58 comprising a casting or welded assembly including an inverted cup-shape cavity 60 having a product and buffer inlet conduit 62 extending at an angle to the cavity 60 and opening therein, is secured to the upper surface of the plunger head 20 by screws 63 or the like. The inlet manifold housing 58 includes a centrally disposed nozzle receiving tube 64 having an internal bore 66 aligned with and opening onto the bore 46 of the plunger head 20. Disposed within the bore 66 of the tube 64 is a media fill system valve assembly 100 constructed in accordance with the present invention.

Figure 3:
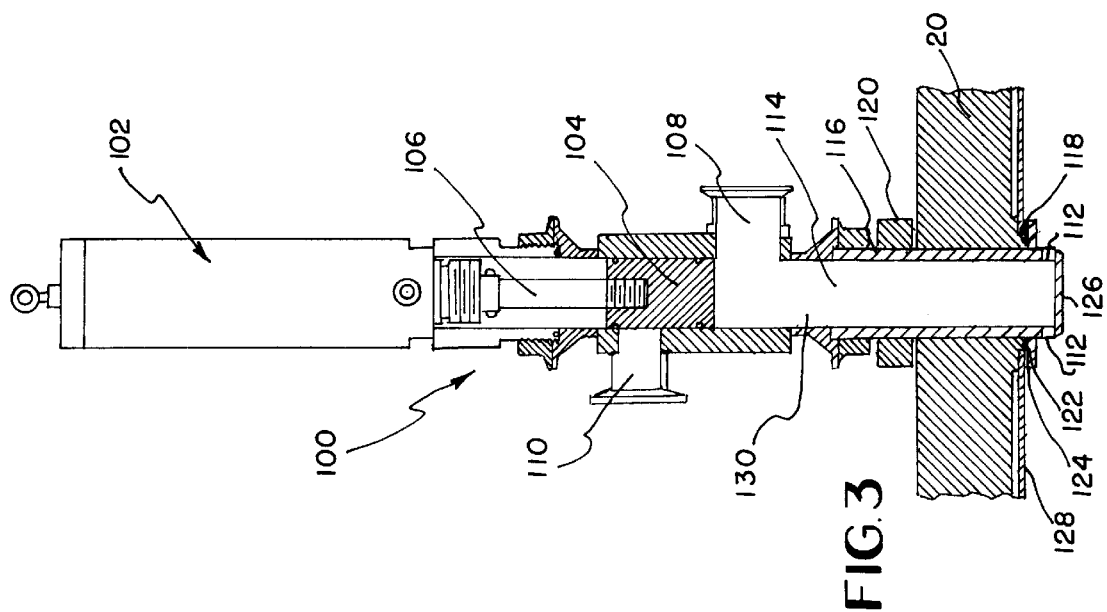
FIG. 3 is an enlarged fragmentary cross sectional view of the media fill section removed and broken away from the chromatography column shown in FIG. 1 in a first position.

FIG. 3 depicts the media filling valve assembly 100 in a first position. This position may be referred to as the pack position or the slurry into column position. The valve assembly 100 is illustrated having a fluid supply, shown as a hydraulic or air cylinder 102, connected to a piston 104 by a connecting rod 106. The air or hydraulic cylinder 102 drives the connecting rod 106 to move the piston 104.

The first position has the piston 104 obscuring flow from the slurry inlet 108 to a clean in place port 110. This first position may be referred to as the packing position. The piston 104 is preferably located just above the slurry inlet 108 when the valve assembly 100 is in the first position. Slurry and/or media may be pumped into the column 10 through at least one, and preferably a plurality, slurry spray ports 112 in an assembly housing 116. More specifically, slurry enters the valve assembly 100 from a supply of slurry at the slurry passage, or slurry inlet 108. From the slurry inlet 108, slurry may proceed into a cavity 114 of the valve assembly 100. Once in the cavity 114, the piston 104 obscures flow to the clean in place port 110. Accordingly, slurry will flow through the cavity 114 to the slurry port or ports 112. The slurry ports 112 are preferably multi-port spray holes, but depending on the particular application, the slurry ports 112 may transfer slurry to one or more other distribution devices.

The cavity 114 of the valve assembly 100 is preferably located at least partly within the assembly housing 116. The assembly housing 116 may connect to the lid, or head 20, of the column 10. One connection system shown utilizes a lip 118 located near a bottom portion of the assembly housing 116 and a valve fixing nut 120 to assist in holding the valve assembly in a fixed manner. Two seals are illustrated as assisting in sealing the assembly housing 116 to the head 20. These seals are a column liquid seal 122 and a resin seal 124. It will be obvious to those skilled in the art that other types of connecting and/or sealing arrangements including a larger or smaller number of seals may be utilized.

In the presently preferred embodiment, a distribution cap 126 directs flow of slurry in directions away from the axis of the central bore 130 of the cavity 114 as the slurry exits the slurry port or ports 112. Additionally a resin screen 128 is illustrated installed in FIGS. 3–5. This resin screen 128 may or may not be present in the embodiment illustrated in FIGS. 1 and 2, however the screen 128 is likely to be present in a fixed bed column type. If the screen 128 is utilized, stainless steel has been found to be an appropriate construction material. The screen 128 may also be referred to by those known in the art as a resin retention screen.

When the column 10 is full of slurry during a filling operation, the operator will be alerted since the pump pumping the slurry in will stall. At this point, the operator may stop the source of slurry into the slurry inlet 108. Looking to FIG. 4, the valve assembly 100 may then be operated such that the piston 104 is moved to the second position. The second position may also be referred to as the run position.

The piston 104 is illustrated as being at or near the distribution cap 126, however this need not necessarily be the case. The fluid source is utilized to pack the slurry in the column 10 when the valve assembly 100 is in the second position by pushing slurry remaining in the cavity 114 into the column through the slurry port or ports 112. Preferably, the piston 104 is stroked from its location above the slurry inlet 108 to a position below the slurry inlet 108. Most preferably, the piston 104 is stroked to at or near the distribution cap 126. As the piston 104 is driven by the cylinder 102 towards the second position, the slurry is compacted in the column 10. As the piston 104 moves through the cavity 114, the slurry will be pushed out the slurry port, or ports 112. This will assist in compacting the slurry in the column 10.

The piston 104 is shown with piston rings 132 which may assist in minimizing, and preferably preventing any fluid flow from the column 10 past the piston 104. For some applications, the valve assembly may be stroked to the second position and back to the first position a number of times in order to force more slurry into the column 10. This process is believed to provide a more compressed bed of resin in the column 10.

While the valve assembly 100 is in the second position, the clean in place port 110 may be open. This will allow the valve a portion of the cavity 114 of the valve assembly 100 to be washed clean. Additionally an open clean in place port may prepare the valve assembly 100 for retracting the piston 104 when necessary. The clean in place port 110 may be open to assist in the movement of the piston 104 from the second to the first or third position. At least in the movement from the second to the first position, an open clean in place port 110 will provide an outlet for any slurry or other material in the cavity 114 or elsewhere in the valve assembly 100. It is also possible that the slurry inlet 108 may be left open to assist in the stroking of the valve assembly from the second to the third or first positions.

FIG. 5 shows the valve assembly 100 in the third position. Some applications may find this placement of the piston 104 useful to assist in cleaning the interior or cavity 114 of the valve assembly 100. The clean in place port 110 is in fluid communication with the slurry inlet 108, and at least a portion of the cavity 114 may be cleaned with the valve assembly 100 in this position.

FIG. 6, which is very similar to FIG. 3, depicts the valve assembly utilized as a slurry outlet valve assembly 200. The valve assembly 200 is illustrated having a fluid supply, shown as hydraulic or air cylinder 202, connected to a piston 204 by a connecting rod 206. The air or hydraulic cylinder 202 drives the connecting rod 206 to move the piston 204.

The operation of the slurry outlet valve 200 again is very similar to that of the media filling valve assembly 100. The position shown in FIG. 6 is the slurry out position. Slurry may be removed from a chromatography column 10 utilizing slurry outlet valve 200. Inlet port 212 provides access to the slurry passage, or slurry outlet 208, for slurry to be removed from the chromatography column 10 when the piston 204 is in the position shown. If the piston 204 is moved closer to the inlet port 212 such that the slurry outlet 208 is no longer in communication with the inlet port 212, the slurry outlet valve 200 will be in a normal operating position. If the piston 204 is positioned closer to the cylinder 202 such that a clean in place port 210 is in communication with the slurry outlet 208, the slurry outlet valve 200 will be in a clean in place position. The operation of the slurry outlet valve in the preferred embodiment may be substantially similar to that of the slurry inlet valve 100 as aforesaid or may be utilized in other ways which would be obvious to one skilled in the art.

Numerous alternations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

What is claimed is:

1. A chromatography column having a container and a valve assembly, said valve assembly comprising:

a valve assembly housing having a cavity elongated along an axis in said housing;

a slurry passage having an inlet opening into said cavity and transversely oriented relative to said axis;

a slurry port in communication with said cavity of the of the valve assembly housing and an interior volume of said container, said slurry passage inlet spaced a distance above said slurry port; and a hydralically operated piston located within said cavity moveable from a first position to a second position; said first position being defined such that said piston is located above the slurry inlet whereby said inlet is in communication with said interoir volume of said container and said second position being defined such that said piston is below said slurry inlet whereby said slurry inlet is closed from communication with said interior volume of said container.

2. The chromatography column of claim 1 wherein the piston is moved by a fluid cylinder, said fluid cylinder connected to the valve assembly housing.

3. The chromatography column of claim 1 further comprising a clean in place port in communication with the cavity of the valve assembly housing, said clean in place port not in communication with the at least one slurry port or the slurry passage when the piston is in the first position, said clean in place port in communication with the slurry passage when the piston is in the second position, said clean in place port not in communication with the at least on slurry port when the piston is in the second position, and said clean in place port in communication with both the slurry passage and the at least one slurry port when the piston is in a third position.

4. The chromatography column of claim 1 wherein the valve assembly housing is secured to a portion of the container by a lip of the housing and a valve fixing nut.

5. The chromatography column of claim 1 wherein the valve assembly housing further comprises a distribution cap, said distribution cap assisting in directing slurry out of the at least one slurry port in a direction substantially transverse to an axis of the cavity of the valve assembly.

6. The chromatography column of claim 1 wherein the slurry passage is a slurry inlet.

7. The chromatography column of claim 1 wherein the slurry passage is a slurry outlet.

8. A chromatography column of claim 1 wherein said piston is located below the slurry passage in the second position.

9. The chromatography column of claim 1 further comprising a clean in place port located a distance above the slurry passage and in communication with the cavity of the valve assembly, and the piston obscuring communication between the clean in place port and the slurry passage when in the first position.

10. A chromatography column comprising:

a container, a head at an upper end of said container, said head having a bore through which a valve is body positioned, said valve body having a cavity opening at a port communicating with an interior volume of said container;

a slurry inlet passage communicating with said cavity;

and a hydraulicly operated piston disposed within said cavity spaced from said inlet passage remote from said interior volume of said container in a first position when said slurry is fed through said slurry inlet passage into the cavity and moveable to a second position intermediate said slurry inlet passage and said container to compress said slurry.

\* \* \* \* \*